United States Patent
Pospisil

[11] Patent Number: 5,125,831
[45] Date of Patent: Jun. 30, 1992

[54] ORTHODONTIC BRACKET WITH BI-DIRECTIONAL HOOK

[75] Inventor: Jirina V. Pospisil, Monrovia, Calif.

[73] Assignee: Minnesota Mining and Manufacturing Company, St. Paul, Minn.

[21] Appl. No.: 608,243

[22] Filed: Nov. 2, 1990

[51] Int. Cl.⁵ ............................................. A61C 3/00
[52] U.S. Cl. ...................................... 433/8; 433/18; 433/19
[58] Field of Search ................. 433/8, 19, 9, 10, 18, 433/11-17

[56] References Cited

U.S. PATENT DOCUMENTS

| | | | |
|---|---|---|---|
| 4,193,195 | 3/1980 | Merkel et al. | 433/13 |
| 4,498,867 | 2/1985 | Kesling | 433/16 |
| 4,545,760 | 10/1985 | Förster | 433/18 |
| 4,820,151 | 4/1989 | Pospisil | 433/17 |
| 5,030,089 | 7/1991 | Kawaguchi | 433/8 |

OTHER PUBLICATIONS

3M Unitek Corporation Catalog (copyright 1990), pp. 1-1 and 1-3 3-7.
Drawings Marked "A" and "B" of Commercially Available Products.
Ortho Organizers, Inc., Advertisement, "Journal of Clinical Orthodontics", Sep. 1989.

Primary Examiner—John J. Wilson
Assistant Examiner—Cindy A. Cherichetti
Attorney, Agent, or Firm—Gary L. Griswold; Walter N. Kirn; James D. Christoff

[57] ABSTRACT

An orthodontic bracket having four tiewings includes a hook which is integrally connected to one of two gingival tiewings. The hook has a mesial notch and a distal notch to provide connection with an elastic member that extends in either direction. The hook also has a flat labial surface for reducing patient discomfort.

8 Claims, 1 Drawing Sheet

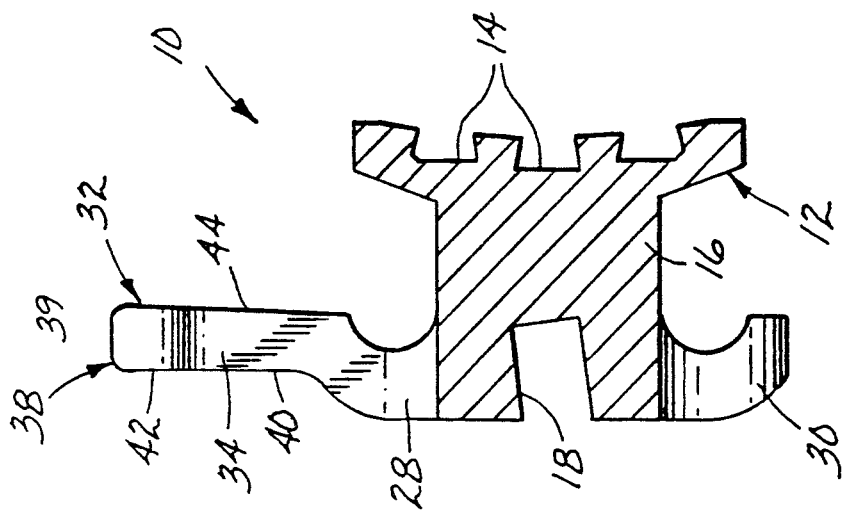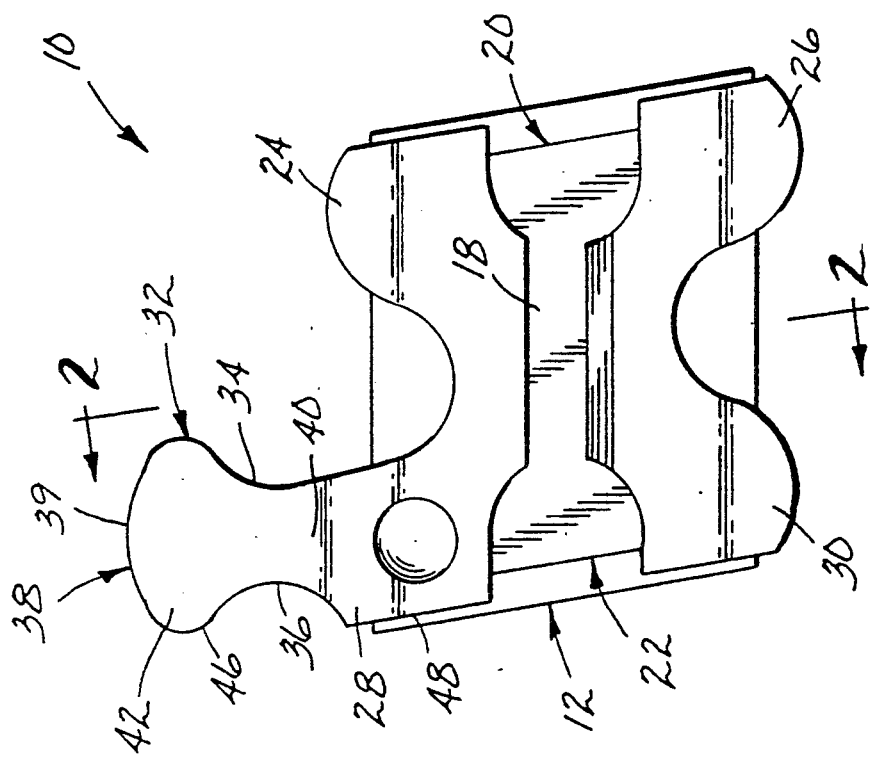

ORTHODONTIC BRACKET WITH BI-DIRECTIONAL HOOK

BACKGROUND OF THE INVENTION

1. Field of the Invention

This invention relates to a bracket that is attached to a tooth for orthodontic treatment.

2. Description of the Related Art

Orthodontic treatment includes the application of mechanical forces to urge the teeth into correct position and proper alignment. Small, slotted bodies known as brackets are secured to the teeth, and a resilient archwire is seated in the bracket slots. The archwire is bent or twisted before installation in the slots in such a manner that the restoring force exerted by the wire tends to shift the teeth into orthodontically correct alignment.

In some instances, the relationship between the upper arch and the lower arch should be changed during orthodontic treatment to correct what are known as Class II or Class III malocclusions. To this end, small hooks are sometimes secured to appropriate brackets, to selected locations of the archwire, or to buccal tubes (which are similar to brackets but which are adapted to be secured to the molar teeth for anchoring the ends of the archwire). An elongated elastic member is connected to a hook on the upper arch and a hook on the lower arch, and has sufficient tension when in place to provide a resilient force in order and urge the upper arch either in an inward or an outward direction relative to the lower arch.

Hooks for correction of Class II and Class III malocclusions are often uni-directional hooks having a generally "J-shaped" configuration, and thus are adapted to hold the elastic member in place only when the member extends in a single predetermined direction which is either a generally mesial, or generally distal direction. However, bi-directional hooks have been sometimes provided in locations near the mid-point of the arch for permitting the elastic member to extend in either the mesial or the distal direction. The bi-directional hook can be initially used to correct a Class II or Class III malocclusion with an elastic member extending in one direction, and subsequently used with an elastic member extending in the opposite direction in order to align the midline of the upper arch with the midline of the lower arch during the final or finishing stages of orthodontic treatment.

In the past, certain bi-directional hooks have been known as ball hooks and include a stem with an enlarged, somewhat hemispherical head. Sometimes, ball hooks are brazed to the archwire or to a tiewing of a bracket. Some brackets made in a sintering operation or in a casting operation have ball hooks that are integrally connected with one of the tiewings of the bracket. However, ball hooks are not entirely satisfactory because the enlarged, hemispherical head often protrudes into the patient's cheeks and causes discomfort.

Occasionally, three-wing orthodontic brackets are used during orthodontic treatment. Three-wing brackets often have two spaced apart occlusal wings on the mesial and distal sides of the bracket, and a single, central gingival wing located in the middle of the gingival side of the bracket. Some three-wing brackets have integral gingival hooks extending from the single, central gingival wing, and the hooks have mesial and distal notches to provide a bi-directional capability. Such hooks are generally flat and have been found to reduce patient discomfort in the areas of the cheeks.

However, some orthodontists prefer twin brackets which have four tiewings rather than three-wing brackets because the brackets with four tiewings provide greater capability for enabling ligatures to exert rotational forces on the tooth about its long axis. Furthermore, brackets with four tiewings provide easier opportunities for using more than one elastic member on the bracket at the same time. As such, there is a need for a bracket having the capabilities of a bracket with four tiewings, but with a bi-directional hook that causes little, if any, patient discomfort.

SUMMARY OF THE INVENTION

The present invention concerns an orthodontic bracket that includes a base having a mesial side and a distal side. Four spaced apart tiewings are connected to the base. The four tiewings consist of a gingival tiewing and an occlusal tiewing next to the mesial side of the base and a gingival tiewing and an occlusal tiewing next to the distal side of the base. A hook is integrally connected to one of the gingival tiewings and extends in a gingival direction. The hook includes a mesially-facing notch and a distally-facing notch. The hook has a terminal end portion with an outer, generally flat labial surface for reducing patient discomfort.

The orthodontic bracket of the present invention provides the versatility of a twin bracket in that the four tiewings provide good rotational control and permit the use of different types of ligation techniques on opposite sides of the bracket. The integral, bi-direction hook permits an interarch elastic member to be first connected to the bracket and extend in one direction for correction of a Class II or Class III malocclusion, and also permits at a later time the use of a elastic member that extends in an opposite direction for correction of midline deficiencies.

BRIEF DESCRIPTION OF THE DRAWINGS

FIG. 1 is a front or labial view of a bracket of the present invention for use with an upper lateral incisor; and FIG. 2 is a cross-sectional view taken along lines 2—2 of FIG. 1 which includes a view of a bi-directional hook of the invention in a distal direction.

DETAILED DESCRIPTION OF THE PREFERRED EMBODIMENT

An orthodontic bracket 10 according to the invention is shown in FIGS. 1 and 2 and includes a base 12 having a contour that matches the contour of a selected tooth. The base 12 of the particular bracket 10 shown in the drawings is for an upper lateral incisor, although brackets for other teeth are also possible.

The base 12 has three dovetail-shaped grooves 14 which extend in a mesial-distal direction. The grooves 14 receive a portion of the adhesive used to bond the base 12 directly to the tooth enamel, and form a strong interlock with the cured adhesive to help retain the bracket 10 on the tooth.

A central portion 16 of the bracket 10 extends from the base 12 in a labial direction, and is formed with an archwire slot 18 that extends in a mesial-distal direction. The base 12 has a mesial side 20 on the right side of the bracket viewing FIG. 1, and a distal side 22 which is located on the left side of the bracket 10 viewing FIG. 1.

Four spaced apart tiewings 24, 26, 28, 30 are integrally connected to the central portion 16 and the base 12, and consist of a gingival tiewing 24 and an occlusal tiewing 26 which are both located next to the mesial side 20. In addition, a gingival wing 28 and an occlusal wing 30 are located next to the distal side 22 of the base 12. As shown in FIG. 2, the tiewing 28 has a gingival section that extends toward the base 14 at an angle relative to the outer labial surface of the tiewing 28.

A hook 32 is integrally connected to the gingival-distal tiewing 28 and extends in a generally gingival direction away from remaining portions of the bracket 10. The hook 32 includes a mesially-facing notch 34 and a distally-facing notch 36 that is located directly opposite the mesial notch 34. The hook 32 has an enlarged terminal end portion 38 having a curved mesial, gingival and distal peripheral edge 39 somewhat in the shape of a partial oval.

The hook 32 has a generally flat wall 40 that extends between the notches 34, 36. In addition, the terminal end portion 38 has a flat labial surface 42 that is generally coplanar with the labial wall 40. As shown in FIG. 2, the hook 32 also includes a lingual flat wall 44 that is generally parallel to the wall 40 and the surface 42. The mesial-distal dimension of the terminal end portion 38 is approximately equal to the overall mesial-distal dimension of the tiewing 28. A distal-most section 46 of the edge 39 is located mesially of a distal-most edge 48 of the tiewing 28.

The hook 32 in areas adjacent the notches 34, 36 and the terminal end portion 38 is recessed inwardly toward the base 12 such that the wall 40 and surface 42 are spaced lingually from the outermost labial surfaces of the tiewings 24–30. As can be observed in FIG. 2, the wall 40 and the surface 42 are generally parallel to the outer labial surfaces of the tiewings 24–30. As such, there is less intrusion of the hook 32 into the patient's cheeks than would otherwise be observed. Moreover, the flat surface 42 along with the rounded peripheral edge 39 of the terminal end portion 38 also reduces the likelihood of patient discomfort.

In use, the bracket 10 is first secured by adhesive to the tooth surface along with other brackets placed on respective teeth, and an archwire is threaded through the bracket slots including the slot 18 of bracket 10. Next, small O-ring elastic ligatures are placed behind the tiewings 24–30 and over the archwire in order to ligate the archwire to the bracket 10. If the tooth needs rotational movement, the ligature may extend only around the two mesial tiewings 24, 26 and the archwire or, alternatively, only around the two distal tiewings 28, 30 and the archwire in order to rotate the tooth about its long axis in the desired direction.

One end of an elongated, elastic member is then placed around the hook 32 and in the mesial notch 34. The other end of the elastic member is then typically placed in a hook of a buccal tube mounted on a molar tooth of the opposite arch. The elastic interarch member urges one arch to move either outwardly or inwardly relative to the other arch in order to correct a Class II or Class III malocclusion as needed.

Once treatment of the Class II or Class III malocclusion is substantially complete, the elastic member is detached from the hook 32. Next, an end portion of another elongated elastic member is placed in the distal notch 36 of the hook 32, the other end of the member is placed about a hook in the opposite arch in order to shift the anterior teeth of one arch relative to the anterior teeth of the other arch for correction of midline deficiencies in instances where the midlines of the two arches do not coincide.

The mesial notch 34 and the distal notch 36 are relatively easy to access by the patient, a particularly desirable feature in instances where the patient is instructed to replace the elastic members as needed. Additionally, the hook 32, being integrally connected with one of the gingival tiewings 24, 28 and having a flattened profile with substantial width in the mesial-distal direction, is not likely to break away from remaining portions of the bracket 10 during use.

I claim:

1. An orthodontic bracket comprising:
   a base having a mesial side and a distal side;
   four spaced apart tiewings connected to said base, said four tiewings consisting of a gingival tiewing and an occlusal tiewing next to said mesial side of said base and a gingival tiewing and an occlusal tiewing next to said distal side of said base; said four tiewings having outer labial surfaces, one of said gingival tiewings having a gingival section extending towards said base at an angle relative to its labial surface; and
   a hook integrally connected directly to said one gingival tiewing and extending in a gingival direction, said hook including a mesially-facing notch and a distally-facing notch, said hook having a terminal end portion with an outer, generally flat labial surface extending generally parallel to said outer labial surfaces of said tiewings for reducing patient discomfort, said hook being recessed inwardly toward said base such that said flat labial surface of said terminal end portion of said hook is spaced lingually from said outer labial surfaces of said tiewings.

2. The bracket of claim 1, wherein said hook includes a generally flat wall extending between said notches.

3. The bracket of claim 2, wherein said wall is generally coplanar with said surfaces.

4. The bracket of claim 1, wherein said one of said gingival tiewings has a distal-most edge, and wherein said hook has a distal-most section located mesially of said edge.

5. The bracket of claim 1, wherein said terminal end portion has a generally oval-shaped configuration.

6. The bracket of claim 1, wherein said terminal end portion has a rounded mesial, gingival and distal peripheral edge.

7. The bracket of claim 1, wherein said hook has a lingual wall that extends in a direction generally parallel to said labial surface.

8. The bracket of claim 1, wherein said one wing has a certain overall mesial-distal dimension, and wherein said outer end portion has a certain overall mesial-distal dimension approximately equal to said dimension of said one wing.

* * * * *